US006302863B1

(12) United States Patent
Tankovich

(10) Patent No.: US 6,302,863 B1
(45) Date of Patent: *Oct. 16, 2001

(54) METHOD FOR REMOVAL OF LIPIDS VIA A PERFLUOROCARBON TUMESCENT SOLUTION

(76) Inventor: Nikolai Tankovich, 9361 Stargaze Ave., San Diego, CA (US) 92129

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/097,993

(22) Filed: Jun. 16, 1998

(51) Int. Cl.[7] ............................ A61B 19/00; A61M 1/00
(52) U.S. Cl. ................................ 604/35; 128/898
(58) Field of Search .................. 604/28, 35, 19, 604/20–21, 22, 902; 606/167; 128/898

(56) References Cited

U.S. PATENT DOCUMENTS

| 4,886,491 | 12/1989 | Parisi et al. ............................. 604/22 |
| 5,052,999 | * 10/1991 | Klein ...................................... 604/19 |
| 5,158,536 | * 10/1992 | Sekin et al. ............................. 604/20 |
| 5,374,624 | * 12/1994 | Segel ...................................... 514/21 |
| 5,414,358 | * 5/1995 | Eilenberg et al. ..................... 324/309 |
| 5,419,761 | * 5/1995 | Narayanan et al. .................... 604/22 |
| 5,423,803 | 6/1995 | Tankovich et al. ....................... 606/9 |
| 5,455,373 | 10/1995 | Kawa ................................... 560/300 |
| 5,472,416 | 12/1995 | Blugerman et al. .................... 604/28 |
| 5,507,790 | * 4/1996 | Weiss ....................................... 600/2 |
| 5,637,318 | 6/1997 | Gross et al. ........................... 424/450 |
| 5,679,459 | * 10/1997 | Reiss et al. ........................ 428/402.2 |
| 5,713,845 | 2/1998 | Tankovich ............................... 604/20 |
| 5,716,318 | * 2/1998 | Manning ................................ 600/16 |
| 5,785,950 | * 7/1998 | Kaufman et al. .................... 424/1.89 |
| 5,884,631 | * 3/1999 | Silberg .................................... 604/22 |
| 5,891,083 | * 4/1999 | Capella et al. .......................... 604/28 |

FOREIGN PATENT DOCUMENTS 0 475 160 B1    3/1992  (EP) .

OTHER PUBLICATIONS

Lippold, B.C., "Depot preparations." Pharmacy International, pp. 60–63 (1980).
Braun–Falco et al., "Liposome Dermatics." Springer–Verlag, Table of contents (1992).
Cevc et al., "Ultraflexible Vesicles, Transfersomes, have an Extremely low pore Penetration Resistance and Transport Therapeutilc Amounts of Insulin Across the Intact Mammalian Skin." Biochimica et Biopysica Acta 1368. pp. 201–215 (1998).
Ostad et al., "Tumescent Anesthesia with a Lidocaine Dose of 55 mg/kg is Safe for Liposuction." Am. Soc. for Dermatol. Surg. 22:921–927 (1996).
Fischer, G., "Liposculture." Am. Soc. for. Derm. Surg. 23: 1183–1187 (1997).
Gregoriadis, G., "Liposome Technology." 2nd ed., vol. 1, Chapter 1, CRC–Press (Boca Raton, FL) pp. 1–36 (1992).
Richards et al., "Temporary Hair Removal in Patients with Hirsutism: A Clinical Study." Cutis 45:199–202 (1990).

(List continued on next page.)

Primary Examiner—Sharon Kennedy
(74) Attorney, Agent, or Firm—Harris F. Brotman; The Brotman Group

(57) ABSTRACT

Compositions of perfluorocarbons and methods of using these compositions for subcutaneous fat removal. A version of the composition also contains local anesthetic and/or vasoconstrictors. The composition is in association with a pharmacuetical carrier. The composition is for use in liposuction techniques. Also provided is a method for subcutaneous removal of lipid or fat cells from a patient using the composition.

9 Claims, 3 Drawing Sheets

OTHER PUBLICATIONS

Hanke et al., "Safety of Tumescent Liposuction in 15,336 Patients." Dermatol. Surg. 21:459–462 (1995).

Illouz, Y.G., "Body Contouring by Lipolysis: A 5 Year Experience with over 3000 cases." Plast. Reconst. Sureg. 72(5):591–597 (1983).

Kharkevich et al., "The use of Magnetic Field for selection transport of curare–like substances." J. Phar. and Toxicology, 5:32–35 (1985).

Klein, J.A., "The Tumescent Technique for Lipo–suction Surgery." Am. J. cosmet. Surg. (4)4:263–267 (1987).

Klein, J.A., "Tumescent Technique for Local Anesthesia Improves Safety in Large–Volume Liposuction." Plast. & Reconst. Surg. 92(6):1085–1098 (1993).

Rohrich et al., "The Role of Subcutaneous Infiltration in Suction–Assisted Lipoplasty: A Review." Plast. & Reconst. Surg. 99(2):514–519 (1997).

Schaefer and Redelmeier, "Skin Barrier, Principles of Percutaneous Absorption." Karger Publication, pp. 146, 198, 214–215 (1996).

Shah and Maibach, "Topical Drug Bioavailability, Bioequivalence, and Penetration." Plenum Press, Chapter 1, 14, 20 (1993).

Urushibata and Kase., "A Comparative Study of Axillar Hair Removal in Women: Plucking v. the Blend Method." J. of Dermatol. 22:738–742 (1995).

Zocchi, M., "Ultrasonic Assisted Lipoplasty: Technical Refinements and Clinical Evaluations." Clin. Plast. Surg. 23(4):575–598 (1996).

Phillipot and Schuber., "Liposomes as Tools in Basic Research and Industry." CRC Press, Index (1994).

Gregoriadis and Neerunjun, "Liposomes and Their Uses in Biology and Medicine." edited by Demetrios Papahadjopoulos, vol. 308, contents page, Sep. 14–16 (1978).

Dean, J.A., "Lange's Handbook of Chemistry," Sec. 10.12, 10.30–10.33 (1992).

Krantz and Carr, "Textbook of Pharmacological Principals of Medical Practive," pp. 26–32 (1964).

Lipowsky, R., "Handbook of Physics of Biological Systems," Elsevier Science, Chap. 9, pp. 441–466 (1995).

Replogle, S.L., Experience with Tumescent Technique in Lipoplasty 17:205–209 (1993).

S.M. Chilaya et al., "Journal of Anesthesiology and Resuscitation," Apr., 1985, pp. 36–40.

Tankovich, N., "Theoretical and Practical Aspects of Magnetosensitive Carrier Development for Transblood–Vessels Drug Targeting," J. of Mendeleev Chemical Society 5:37–42 (1987).

* cited by examiner

METHOD FOR REMOVAL OF LIPIDS VIA A PERFLUOROCARBON TUMESCENT SOLUTION

BACKGROUND OF THE INVENTION

1. Field of the Invention

This invention relates to a composition of matter for dissolving of fat associated with or near the skin and a method of using the composition in combination with a high frequency oscillator for removal of the fat. In particular, the composition is directed to a perfluorocarbon composition.

2. Description of Related Art

A major concern relating to human skin is the accumlulation of excess layers of fat cells, especially in middle age and elderly people, which causes them to appear fatty and older.

Recent attempts have been made to remove subcutaneous fat as well as treat cellulite utilizing different techniques. Celluite is a lay term describing the uneven, bumpy texture of skin in specific areas of the female body (primarily hips, thighs, and buttocks) caused by the abnormal accumulation of fatty cells in masses beneath the skin. The main method today for subcutaneous fat removal is liposuction, a method which presents potential risk to the patient.

One of the first comprehensive reports on liposuction appeared in 1983 (Y. G. Illouz, Body Contouring by Lipolysis: A 5-Year Experience with over 300 cases; Plast. Reconst. Surg. 72:591 (1983)). A breakthrough ocurred with the development of the tumescent technique of Jeffrey Klein (Plast. Reconstr. Surg., 92:1085 ((93)). Tumescent anesthesia allows liposuction to be performed over larger areas using local anesthesthetic and a vasoconstrictor in a solution injected in the desired location. U.S. Pat. No. 5,472,416 by Blugerman et al. describes the tumescent lipoplastic method and apparatus. Ultrasonic tumescent liposuction was developed by Dr. Michele Zocchi in 1992 (Clin. Plast. Surg (1996) pp. 575–598). Ultrasound at 1 Mhz with power of 2 W/cm$^2$ is applied to the skin for ten minutes before suction, which is described by Parisi et al. in U.S. Pat. No. 4,886,491. Ultrasound from 16 to 20,000 Hz alters adipose tissue through mechanical disruption and cavitation with minimal thermal effect. Another method for removal of subcutaneous fat involves vaporization of adipose tissue using a laser.

Complications and trauma are major problems with the above methods for removal of subcutaneous fat and treatment of cellulite by liposuction. Excessive bleeding is associated with the procedure because the tools which are inserted into the subcutaneous fat are either sharp knives or blunt canulas that are scraped through the site of interest, damaging blood vessels. Complications arise mostly due to damaged blood vessels, causing blood clots that express as irregularities in the overlying skin. Nerves are also affected by the traumatic aspects of the procedure, causing loss of feeling in the treated area for some months afterwards.

DISCLOSURE OF THE INVENTION

The present invention, which overcomes these problems and inefficiencies of subcutaneous fat removal, is directed to compositions of perfluorocarbons and methods of using these compositions for subcutaneous fat removal. The advantage provided by the compositions and method of the invention is based on the ability of perfluorocarbons to rapidly emulsify the fat in the adipose cells without the necessity of a cannula or other blunt or sharp instrument to mechanically break, tear, or otherwise disconnect the adipose cells from site of intersest. Emulsification of the fat in the adipose tissue obviates the use of a cannula or other blunt or sharp instrument to mechanically break, tear or otherwise disconnect the adipose cells from the site of interest. In the present invention, emulsified fat is easily drawn out of the body by suction without the trauma caused by the presently available techniques of liposuction.

In one aspect, the invention is directed to a composition comprising perfluorocarbon and one or more agents selected from the group consisting of anesthetics and vasoconstrictors. The composition is in association with a pharmacuetical carrier.

It is an object of the invention to provide a composition for use in techniques, in particular liposuction techniques, for removal of tissue and fat from a patient.

Another aspect of the invention is a method for subcutaneous removal of lipid or fat cells from a patient. The method comprises the steps of contacting subcutaneous lipid or fat cells in an area of the patient with an effective or sufficient amount of the composition of the invention for a sufficient period of time to emulgate the lipid or fat cells into an emulsion. The emulsion is removed in a subsequent step. A version of the method involves oscillating the lipid or fat cells which were contacted with the composition with a sufficient amount of oscillation energy to enhance emulgation of the fat compared to emulgation without oscillation.

It is an object of the invention to provide a tumescent solution which emulsifies skin fat, forming it into a suspension, emulsion or liposomes in the presence of high frequency oscillations suitable for removal by suction without damage to blood vessels.

Another object of the invention is to provide a method of removal of fat from a patient with no damage or minimal damage to blood vessels.

These and many other features and attendant advantages of the present invention will become better understood by reference to the following detailed description of the invention when taken in conjunction with the accompanying drawings.

MODES OF CARRYING OUT OF THE INVENTION

General Description and Definitions

The practice of the present invention will employ, unless otherwise indicated, conventional techniques in cosmetic or aesthetic surgery, including liposuction, and medicinal chemistry and medicinal formulation within the skill of the art. Such techniques are explained fully in the literature. See, e.g. Ronrich, R. J., Beron, S. J., Fodor, P. B., The Role of Subcutaneous Infiltration in Suction-Assisted Lipoplasty: A review. Plast. Reconstr. Surg. (1997) 99:514–519: Hanke, C. W., Bernstein, G., Bullock, S., Safety of Tumescent Liposuction in 15,336 Patients, Dermatol. Surg. (1995) 21:459–462; Zocchi, M. L. Ultrasonic Assisted Lipoplasty: Technical Refinements and Clinical Evaluations, Clin. Plast. Surg. (1996):pp. 575–598).

The following terminology will be used in accordance with the definitions set out below in describing the present invention.

As used herein, the term "perfluorocarbons" (PFCs) means a fluorocarbon in which the hydrogen directly attached to the carbon atoms is completely replaced by fluorine; PFC's are compounds with a highly developed active surface having the capacity to bind lipids in an emulsion, and thereby breakdown skin fat. Topically applied oscillation or vibration enhances the capacity of PFCs to emulsify the fat. The scope of structures included in PFCs used in the present invention are illustrated, but not limited to those in U.S. Pat. Nos. 5,455,373; 5,637,318; and 5,679,459 which are incorporated by reference.

As used herein, the term "emulgate" means to form an emulsion.

As used herein, the term "tumescent technique" means a technique for liposuction which involves the infiltration of a "tumescent solution." A tumescent solution contains a local anesthetic agent, e.g. lidocaine, and a vasoconstrictor, e.g. epinephrine, in a pharmaceutical carrier which is infiltrated into the subcutaneous fat typically in a liposuction surgical procedure through a cannula or through a needle, in some procedures with the aid of a perstaltic pump. The vasoconstrictor and local anesthetic agent of the tumescent solution, respectively, reduce bleeding and eliminate the need for general anesthetics. The usefulness of prior art tumescent solutions used in prior art liposuction techniques is limited, however, because of excess bleeding from trauma to blood vessels caused by the cannula (blunt or sharp-edged) as it is scraped through the subcutaneous site of interest and sucks out adipose tissue and fat.

Figure 1:
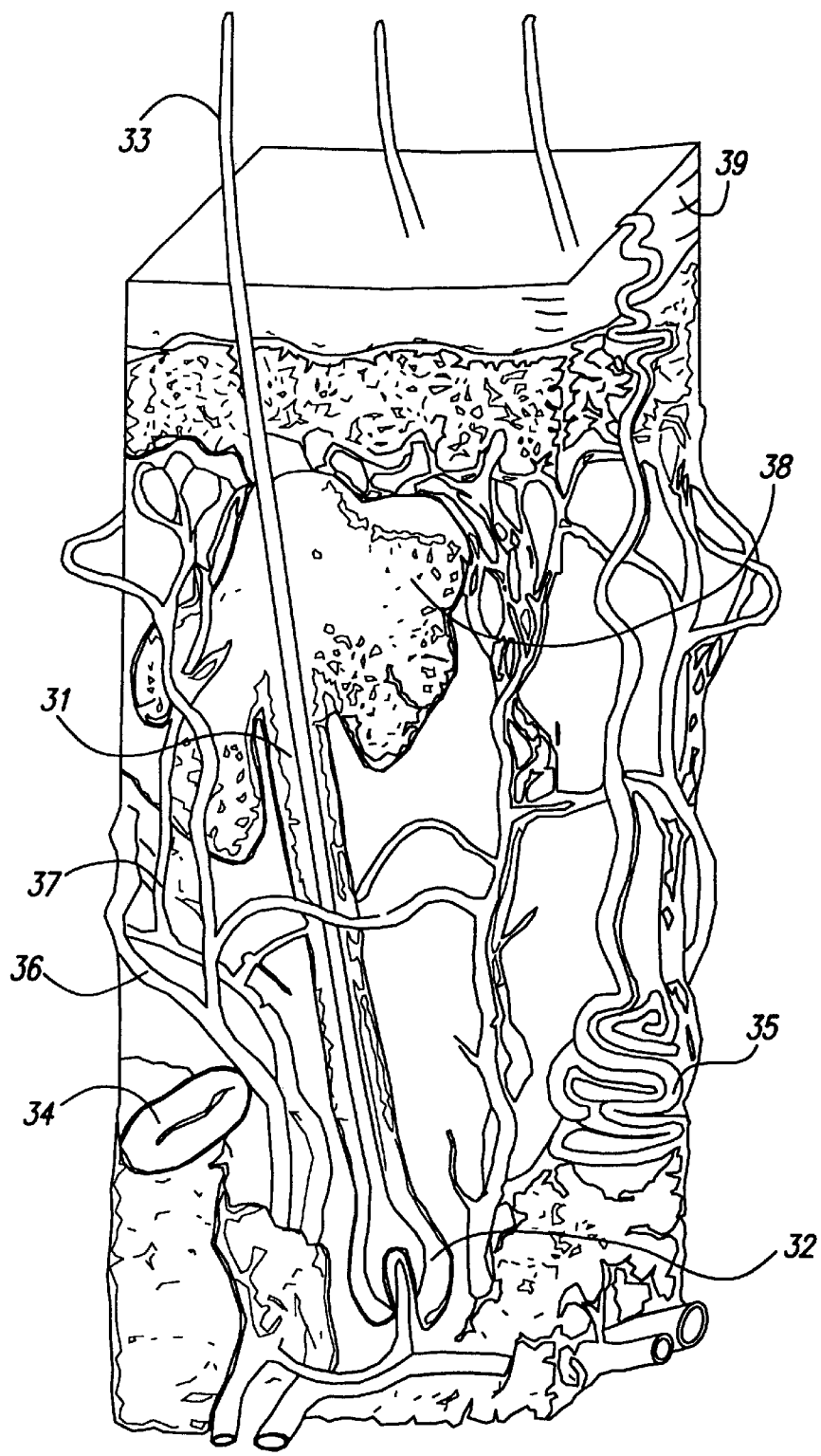
FIG. 1 is a diagram of a section of skin.
Figure 2:
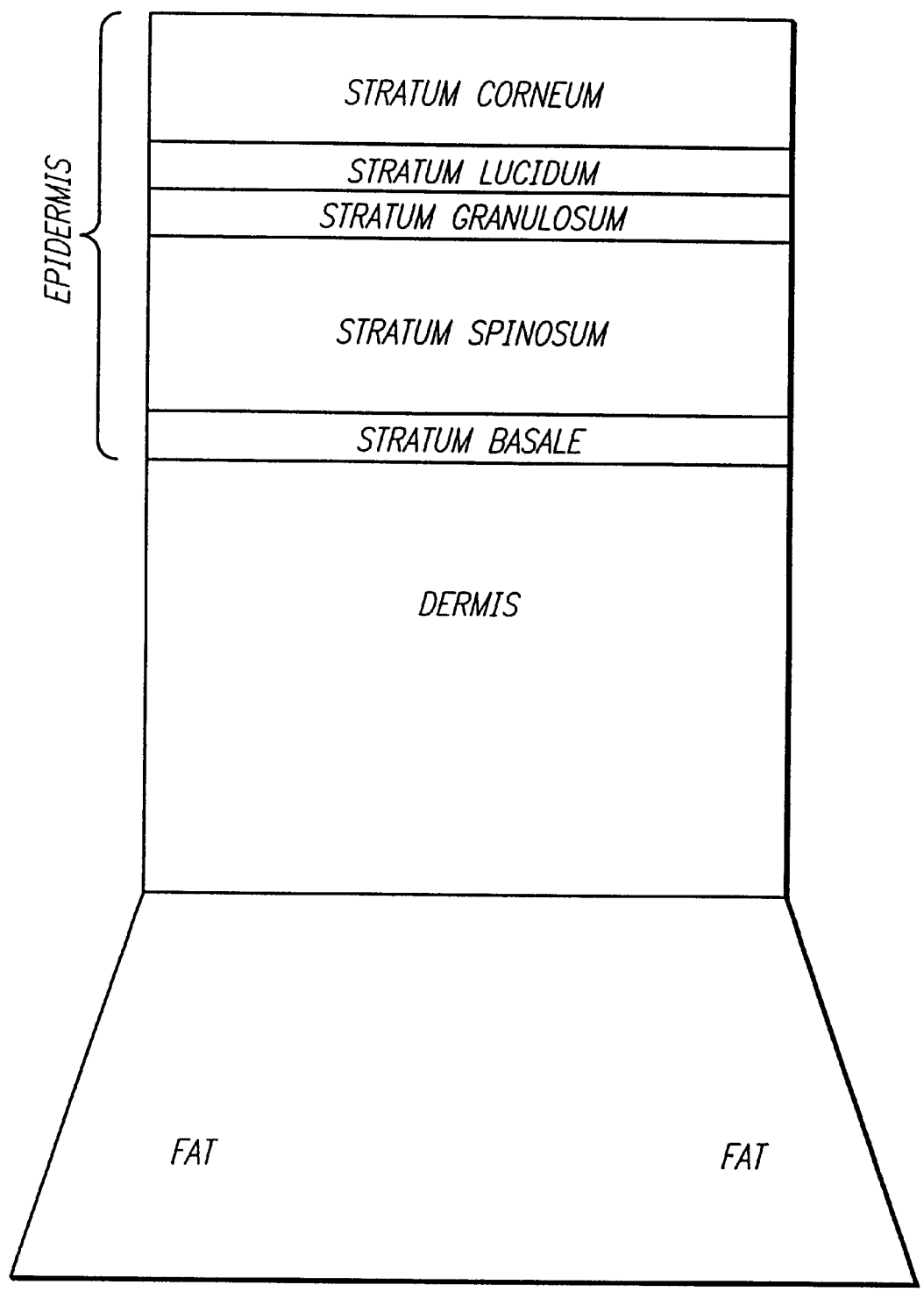
FIG. 2 is a block diagram of the tissue layers of skin.

The advantages provided by the present invention will be better understood with reference to FIG. 1, which is a cross section of human skin showing the location of fat and blood vessels. FIG. 1 illustrates epidermis, dermis and subcutaneous fat with the hair shaft 33 of a hair growing in a hair duct 31 from dermal papilla 32. Also shown is a nerve ending 34, a sweat gland 35, a sebaceous gland 38, arteries 36, and veins 37. Subcutaneous fat or lipid is predominated with adipocytes, i.e. fat cells which contain cytoplasmic lipids. The subcutaneous fat is both a cushion to prevent mechanical injury as well as a storage depot for high-potency energy sources. Fat is stored in adipocytes, which are enormously distended cells that comprise the majority of cells in adult adipose tissue. The composition and method of the invention provide an effective amount of perfluorocarbon which, in contact with the adipocytes and, in due course, in contact with the fat within the adipocytes at the site of interest, emulgages the fat stored in the adipocytes.

Adipocytes are arranged in sheet-like lobules separated by thin, fibrous septa in which blood vessels supply nutrients. These septa anchor the deepest limits of the reticular dermis to underlying fascia, with an intervening cushion of subcutaneous lobules formed by masses of adipocytes. The blood vessel-rich septa are ripped, broken and otherwise traumatized by conventional liposuction techniques using conventional tumescent solutions.

Composition of the Invention

The present invention provides a composition for use in the removal of tissue and fat from a patient. The composition comprises a perfluorocarbon (PFC) and one or more agents selected from the group consisting of anesthetics and vasoconstrictors. The composition can be combined with a pharmaceutical carrier, preferably a pharmaceutical carrier suitable for cosmetic or aesthetic surgical procedures, in particular liposuction, for removal of body fat. Compositions used in the art for such procedures as known as "tumescent solutions."

It is understood that the PFC of the composition is selected from one or more of the group of PFCs consisting of one or more aliphatic straight-chain and branched fluoroalkanes, mono-or bicyclic and optionally fluoralklysubstituted flurocycloalkanes, perfluorinated aliphatic or bicyclic amines, bis(perfluoroalkl) ethenes; or alternatively from one or more substituted and unsubstituted alkyl, alkenyl, alkynyl, alkoxyl groups which can have straight or branched chains, ring structures including single or fused ring structures, e.g. phenyl, or naphthyl. The unsaturated groups can have a single site of unsaturation or a plurality of sites of unsaturation. Fluorocarbon compostions such as Perftoran™ and perflubron™, are included.

Medically useful PFCs and syntheses thereof are disclosed in U.S. Pat. Nos. 5,455,373; 5,637,318; and 5,679,459 which are incorporated by reference. The scope of PFCs that find use in the present invention is illustrated but not limited by the PFC structures disclosed therein. Guidance for formulating compositions comprising PFCs is also disclosed therein, and further disclosed in Dean, J. A. Lange's Handbook of Chemistry, (1992), Sections 10.12, 10.30–10.33.

Combined with an anesthetic and/or a vasoconstrictor, and a pharmaceutical carrier, the composition of the invention provides a tumescent solution. The amount of PFC in the composition is in the range from about 0.1% to about 100% w/v, preferably in the range from about 10% to about 70%. A particularly preferred range is from about 50% to about 65%. Pharmaceutical carriers, particularly for cosmetic surgical procedures, are well known in the art, and include but are not restricted to solutions, emulsions, transferosomes (Krantz and Carr, Textbook of Pharmacological Principals of Medical Practice, (1964), pp. 26–32; Lippold, B. C. Pharmacy International (1980) 3:1–60; Gregoriadis, G. and Neerunjun, D. E., Liposomes and Their Uses in Biology and Medicine (1977), pp. 14–16.

Methods for making tumescent solutions are well known in the art (Ostad, A., Kageyama, N., Moy, R. L., Tumescent Anesthesia with a Lidocaine Dose of 55 mg/kg Is Safe for Liposuction, Dermatol. Surg. (1996) 22:921–927; Replogle, S. L., Experience With Tumescent Technique in Lipoplasty (1993) 17:205–209. Accordingly, the amount of anesthetic and/or vasoconstrictor for use in the compositions of the invention are readily determined by one of ordinary skill in the art. Furthermore, methods are well known in the art for determining the efficacy of a tumescent solution of the invention (Klein, J. A., The Tumescent Technique for Liposuction Surgery, Am. J. Cosmet. Surg. (1987) 4:263–267.

Vasoconstrictors which are usefull in the composition of the invention include but are not restricted to epinephrine, levarterenol, phenylephrine, athyladrianol, ephedrine.

Anesthetics which are useful in the composition of the invention include but are not restricted to lidocaine, marcaine, nesacaine, diprivan, novocaine, ketalar, xylocaine.

EXAMPLE 1

Tumescent Solution

A preferred tumescent solution is a composition which comprisies the PFC Perftoran™, a vasoconstrictor, and an anesthetic. Perftoran™ is obtained from Pharmpreparaty Company, Russia.

Perftoran™ contains 12 mEq of sodium carbonate per liter, 15.2% perfluorodecalin, 7.6% perfluoromethylcyclohexypiperidin, 4% Proxanol-268, 0.039% potassium chloride, 0.6% sodium chloride, 0.019% magnesium chloride, 0.028% calcium chloride, 0.13% sodium hydrocarbonate, 0.02% sodium hydrophosphate, 0.2% glucose, the remainder being water.

Accordingly, the preferred tumescent solution is a mixture of 5% by volume 2% lidocaine (total 0.1% in solution), 1% epinephrine, and Perfotoran. The tumescent solution is directed into the site of interest where lipids need to be extracted.

METHOD OF THE INVENTION

In another aspect, the invention is directed to a method for subcutaneous removal of lipid from a patient. The method comprises the step of contacting the subcutaneous lipid with an effective or sufficient amount of a composition comprising PFC for a sufficient period of time to emulgage the lipid into an emulsion. Another step involves removing the emulsion from the patient. A preferred version of the method involves administering oscillation to the lipid after the PFC is in contact with the lipid for a sufficient period of time. A sufficient amount of oscillation is administered to speed up or enhance emulgation so that more emulsion is formed than without oscillation.

In one aspect, the method involves contacting the lipid with a composition of PFC, preferably a composition of PFC in a pharmaceutical carrier. The amount of PFC in the composition is in the range of about 50% to about 80%.

In yet another aspect, the compostion of PFC further comprises one or more agents selected from the group consisting of anesthetics and vasoconstrictors, and preferably in assocation with a pharmaceutical carrier to form a tumescent solution. The amount of PFC in the composition as well as amounts of vasoconstrictor and local anesthetic are as described above for the compositions of the invention.

As described above, methods in the art are well known for making tumescent solutions, determining their efficacy, and determining the optimal periods of time for contact between the compositions and the fat in the site of interest. Furthermore, methods are also well known in the art for applying oscillation to areas of concern, determining a sufficient amount of time to apply oscillation to the area of concern, and for measuring the efficacy of the oscillation energy for enhancing the emulgation.

Figure 3:
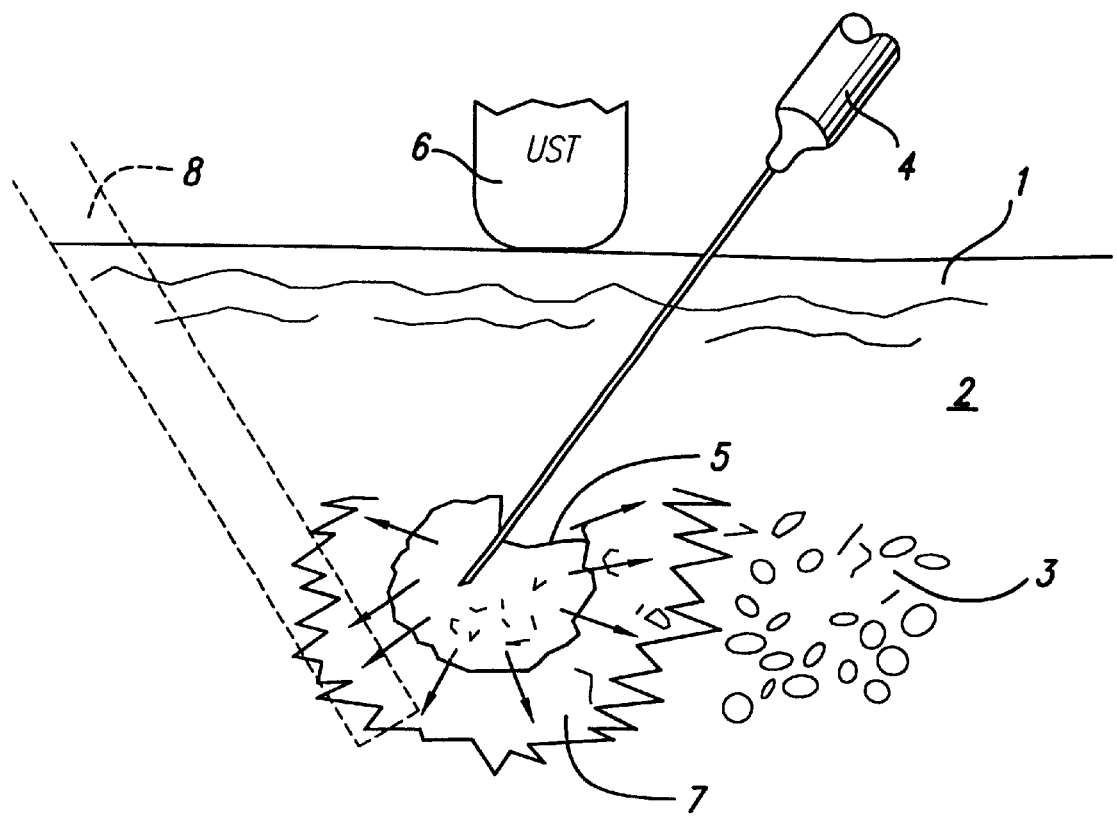
FIG. 3 illustrates skin fat liposuction using perfluorocarbons and an oscillator.

The step of contacting subcutaneous lipid with a sufficient amount of a composition comprising perfluorocarbon can be achieved by administering the composition to the area of concern with a cannula or by injection with a needle (FIG. 3). FIG. 3 shows a syringe (4) containing the composition of the invention inserted through the epidermis (1), projecting down into the dermis (2) where subcutaneous fat (SCF) (3) is located in order to contact the subcutaneous lipid in the site of interest with a suffcient or effective amount of the composition for a sufficient period of time to emulgate the lipid into an emulsion. An ultrasonic transducer (UST) (6) applies oscillation to the SCF or lipid in the adipocytes. The step of removing the emulsion can be achieved by aspirating with a cannula or needle (8). The steps of contacting and removing comprise the well known surgical procedure of liposuction These techniques are well known in the art, as disclosed in U.S. Pat. No. 5,472,416, incorporated by reference, and in Fisher, G., Liposculpture in J. Derm. Surg. (1997) pp. 1183–1187.

In a preferred aspect of the method, after the step of contacting the lipid at the site of interest with the composition of the invention, oscillations, i.e. the mechanical vibrations of high frequency are topically applied to promote emulgation, i.e. to enhance the process of the fat molecules binding to the PFC and emulsification, i.e., dissolving of fat molecules. The suspension or emulsion is sucked out without blood vessel damage, a major advantage of the invention. Ultrasonic instruments and methods for applying oscillation to the lipid in a patient in an area of concern are known in the art, as disclosed in U.S. Pat. Nos. 5,419,761 and 4,886,491; and in M. Zocchi, Clin. Plast. Surg. (1996) pp. 575–598.

Having thus described exemplary embodiments of the present invention, it should be noted by those skilled in the art that the disclosures herein are exemplary only and that various other alternatives, adaptations and modifications may be made within the scope of the present invention. Accordingly, the present invention is not limited to the specific embodiments as illustrated herein, but is only limited by the following claims.

What is claimed is:

1. A method for removal of subcutaneous lipid in a patient at a site of interest, said method comprising the steps of:
   (a) contacting subcutaneous lipid in the site of interest with a sufficient amount of a composition comprising perfluorocarbon for a sufficient period of time to emulgate the lipid into an emulsion; and
   (b) removing said emulsion.

2. The method of claim 1 wherein said composition comprising perfluorocarbon further comprises one or more agents selected from the group consisting of anesthetics and vasoconstrictors.

3. The method of claim 2 wherein said composition is in association with a pharmaceutical carrier.

4. The method of claim 2 wherein said perfluorocarbon is selected from one or more of the group consisting of aliphatic straight-chain and branched fluoroalkanes, mono- or bicyclic and optionally fluoralkly-substituted flurocycloalkanes, perfluorinated aliphatic or bicyclic amines, bis(perfluoroalkl) ethenes.

5. The method of claim 2 wherein said perflurorcarbon is selected from one or more of the group consisting of substituted and unsubstituted alkyl, alkenyl, alkynyl, alkoxyl groups which can have straight or branched chains, ring structures including single or fused ring structures, e.g. phenyl, or naphthyl, wherein the unsaturated groups can have a single site of unsaturation or a plurality of sites of unsaturation.

6. The method of claim 2 wherein said anesthetic is selected from one or more of the group consisting lidocaine, marcaine, nesacaine, diprivan, novocaine, ketalar, and xylocaine.

7. The method of claim 2 wherein said vasoconstrictor is selected from one or more of the group consisting of epinephrine, levarterenol, phenylephrine, athyladrianol, ephedrine.

8. The method of claim 1 wherein step (a) further comprises contacting said lipid with a sufficient amount of oscillation to emulgate more of said lipid than emulgated without oscillation.

9. The method of claim 1 wherein said contacting and removing steps comprise a liposuction surgical procedure wherein said composition is administered to the site of concern with a cannula or by injection with a needle and said emulsion is removed from said site of interest by aspiration through a cannula or needle.

* * * * *